United States Patent [19]

Meul

[11] Patent Number: 5,227,513
[45] Date of Patent: Jul. 13, 1993

US005227513A

[54] ACETYLSALICYLOYL-L-CARNITINE AND PROCESS FOR ITS PRODUCTION

[75] Inventor: Thomas Meul, Visp, Switzerland

[73] Assignee: Lonza Ltd., Gampel/Valais, Switzerland

[21] Appl. No.: 833,673

[22] Filed: Feb. 11, 1992

[51] Int. Cl.⁵ .............................................. C07C 69/76
[52] U.S. Cl. ...................................................... 560/66
[58] Field of Search ........................................ 560/66

[56] References Cited
PUBLICATIONS

Okabe et al., Japan. J. Pharmacol., 24, (1974), pp. 363 to 371.
Chaumontet et al., Arzneimittelforschung [Pharmaceutcal Agent Research], 28, (1978), pp. 2119 to 2121.

Primary Examiner—Paul J. Killos
Attorney, Agent, or Firm—Fisher, Christen & Sabol

[57] ABSTRACT

Acetylsalicylic acid esters of carnitine are distinguished relative to acetylsalicylic acid. The esters can be produced by acetylation of suitable salicylic acid esters of carnitine.

13 Claims, No Drawings

ACETYLSALICYLOYL-L-CARNITINE AND PROCESS FOR ITS PRODUCTION

BACKGROUND OF THE INVENTION

1. Field Of The Invention

The invention relates to 3-(2-acetoxybenzoyloxy)-4-(trimethylammonio)butyric acid betaine acetylsalicyloyl-L-carnitine of formula:

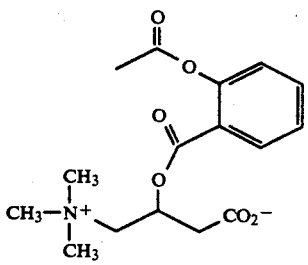

in its racemic form and optically active forms, and its pharmaceutically acceptable salts as well as a process for its production. 3-(2-Acetoxybenzoyloxy)-4-(trimethylammonio)butyric acid betaine is a salicyl acid derivative with therapeutic properties as an ester of acetylsalicylic acid with carnitine (acetylsalicyloyl-carnitine).

2. Prior Art

Salicylic acid is used in the form of its acetyl derivative to a large extent as an analgesic. Although this acetyl derivative (known, i.a., as Aspirin ®) was originally developed to reduce disturbing side effects of the salicylic acid already known earlier, nevertheless, it is affected by several properties which limit its possibilities of use. Above all, its low water solubility, in particular in an acid medium, for example, in gastric juice, is one of these unfavorable properties. With oral administration of aqueous solutions, the low solubility can lead to the precipitation of the active ingredient in the stomach. This effect is undesirable not only in individuals with a sensitive or previously damaged gastric mucous membrane, since it can lead to serious side effects in these individuals, but it quite generally slows down the resorption and, thus, also the beginning of the analgesic action.

Moreover, acetylsalicylic acid can be administered practically only orally, but not parenterally, for example, intravenously, intraperitoneally or topically. But precisely because of the quick onset of action and/or the gentle treatment of the gastrointestinal tract, a parenteral administration would often be desirable.

BROAD DESCRIPTION OF THE INVENTION

The main object of the invention was to provide a salicylic acid derivative, which is also readily water-soluble in the acid range, is easily resorbed, exhibits a lowest possible toxicity and can be administered both enterally and parenterally or topically and shows a quickly starting analgesic action in all forms of administration. The main object of the invention is achieved: by 3-(2-acetoxybenzoyloxy)-4-(trimethylammonio)-butyric acid betaine:

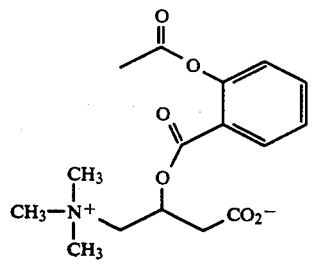

and the pharmaceutically acceptable salts thereof; by (R)-(—)-3-(2-acetoxybenzoyloxy)-4-(trimethylammonio)-butyric acid betaine:

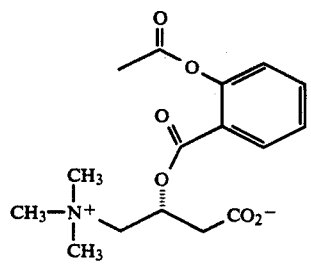

and the pharmaceutically acceptable salts thereof; and by (S)-(+)-3-(2-acetoxybenzoyloxy)-4-(trimethylammonio)-butyric acid betaine:

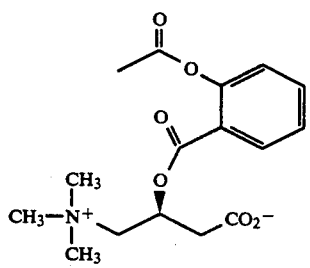

and the pharmaceutically acceptable salts thereof.

Other objects and advantages of the invention are set out herein or are obvious herefrom to one skilled in the art. The other objects and advantages of the invention are achieved by the compounds and process of the invention.

The invention also involves the process of administering a pharmaceutical composition containing: 3-(2-acetoxybenzoyloxy)-4-(trimethylammonio)-butyric acid betaine or its pharmaceutically acceptable salts as the therapeutically active ingredient; or (R)-(—)-3-(2-acetoxybenzoyloxy)-4-(trimethylammonio)-butyric acid betaine or its pharmaceutically acceptable salts as the therapeutically active ingredient; or (S)-(+)-3-(2-acetoxybenzoyloxy)-4-(trimethylammonio)-butyric acid betaine or its pharmaceutically acceptable salts as the therapeutically active ingredient. The pharmaceutical composition can be for humans or non-human animals.

The invention also involves the process of administering a pharmaceutical composition containing: 3-(2-acetoxybenzoyloxy)-4-(trimethylammonio)-butyric acid betaine or its pharmaceutically acceptable salts as an analgesic which is gentle to the gastric mucous membrane; or (R)-(—)-3-(2-acetoxybenzoyloxy)-4-(trimethylammonio)-butyric acid betaine or its pharmaceutically acceptable salts as an analgesic which is gentle to the gastric mucous membrane; or (S)-(+)-3-(2-acetoxybenzoyloxy)-4-(trimethylammonio)-butyric acid betaine or its pharmaceutically acceptable salts as an analgesic which is gentle to the gastric mucous membrane. The pharmaceutical composition can be for humans or non-human animals.

The invention further involves a process for the production of 3-(2-acetoxybenzoyloxy)-4-(trimethylammonio)-butyric acid betaine. The process includes acetylating a 3-(2-hydroxybenzoyloxy)-4-(trimethylammonio)-butyric acid betaine. Preferably acetyl chloride or acetic anhydride in the presence of catalytic amounts of $H_2SO_4$ is used as the acetylation agent. Preferably the acetylation is performed at a temperature between 40° C. and 100° C.

DETAILED DESCRIPTION OF THE INVENTION

The invention includes the 3-(2-acetoxybenzoyloxy)-4-(trimethylammonio)-butyric acid betaine. The betaine compound comprises an asymmetrical carbon atom and can, therefore, occur in two mirror image, optically active forms and as a racemic mixture. Here, the enantiomer with (R)-configuration, which is derived from the naturally occurring L-carnitine, is preferred. But the advantageous physical-chemical properties, such as, high water solubility and advantageous pH of the solution, are also achieved by the (S)-enantiomer and the racemate. However, L-carnitine is known as an acyl group carrier in lipo-metabolism. It is actively taken up by highly affine transport systems in most organs of the body and by antiport transporters in cellular organelles (mitochondria, etc.). It is to be expected that acetylsalicyloyl-L-carnitine is also taken up in cells and organelles by these transport systems and, thus, the onset of action is even accelerated.

Acyl-L-carnitines are further easily cleaved by cell-specific enzymes, so that a quick release of the salicylate radical is to be expected.

Tests in rats showed an extremely low acute toxicity of acetylsalicyloyl-L-carnitine. Doses up to 1000 mg/kg of body weight were easily orally tolerated and no harmful side effects were observed in intravenous and intraperitoneal administration of therapeutic amounts.

Of course, it is also within the scope of the invention to form salts of the acetylsalicyloyl-carnitine with pharmaceutically acceptable acids and to use the compound in this form.

The acetylsalicyloylcarnitine is produced according to the invention by acetylation of salicyloylcarnitine. As the acetylation agent, acetylchloride or acetic anhydride in the presence of catalytic amounts of $H_2SO_4$ is especially suitable. The acetylation suitably takes place in a temperature range of 40° and 100° C. in the presence of acetic acid as a solvent. Experience shows that acetylsalicyloylcarnitine can be obtained after the usual working up in a good yield and a high purity after a reaction time of about 5 hours.

Also, it is within the scope of the process according to the invention to then convert the betaine to a corresponding salt by adding a pharmaceutically acceptable acid.

The following example illustrates the performance of the production process according to the invention.

EXAMPLE

Acetylsalicyloyl-L-carnitine.HCl 0.95 g of salicyloyl-L-carnitine.HCl ($[a_D^{20}= -31.2°$ (c=1, $H_2O$); melting point: 185° to 187° C.) was mixed with 2.35 g of acetyl chloride and 5.0 ml of acetic acid, and heated for 5 hours to 60° C. Then the reaction mixture was concentrated by evaporation in a vacuum and the residue was suspended in 10.0 ml of ethyl acetate. The crystalline product was washed with 5.0 ml of ethyl acetate and dried in a vacuum at 40° C. 0.95 g of white, crystalline acetylsalicyloyl-L-carnitine.HCl with a melting point of 154° to 158° C. was obtained. Other properties of the product were:

| | |
|---|---|
| $^1$H-NMR (DMSO-$d_6$, 300 MHz)δ = | 12.9 (br.s, 1H), |
| | 8.04 (d, 1H, J=1.9Hz), |
| | 7.73 (t, 1H, J=7.5Hz), |
| | 7.46 (t, 1H, J=7.6Hz), |
| | 7.28 (d, 1H, J=8.0Hz), |
| | 5.70 (m, 1H), |
| | 4.08–3, 83 (m, 2H), |
| | 3.20 (s, 9H), |
| | 2.93–2, 78 (m, 2H), |
| | 2.33 (s, 3H); |
| $[a]_D^{20} = -4.17°$ (C = 1, $H_2$) | |

STOMACH TOLERANCE TESTS IN RATS (ULCER INDEX)

R-(−)-3-(2-Acetoxybenzoyloxy)-4-(trimethylammonio)-butyric acid betaine.HCl (acetylsalicyloyl-L-carnitine=ASC) was tested in male rats in comparison with acetylsalicylic acid (ASA) by gastric mucous membrane changes being induced according to the methods of Okabe et al., Japan. J. Pharmacol., 24, (1974), pages 363 371. The test substances were administered p.o. in a 1 percent carboxymethyl cellulose suspension (1 percent CMC) to the test rats. The gastric mucous membrane changes were measured by the Ulcer Index according to Chaumontet et al., Arzneimittelforschung [Pharmaceutical Agent Research], 28, (1978), pages 2119 to 2121.

Table 1 describes the test results:

TABLE 1

| Substance | Ulcer Index (U.I.) | Number of rats |
|---|---|---|
| Comparison, 1% CMC 1 ml/250 g | 63.00 | 10 |
| Comparison, ASA 200 mg · $kg^{-1}$ | 300.00 | 20 |
| Invention, ASC 200 mg · $kg^{-1}$ | 170.00 | 10 |
| Invention, ASC 500 mg · $kg^{-1}$ | 190.00 | 10 |
| Invention, ASC 1000 mg · $kg^{-1}$ | 220.00 | 10 |

CMC = carboxymethyl cellulose
ASA = acetylsalicylic acid
ASC = acetylsalicyloyl-L-carnitine · HCl

What is claimed is:

1. 3-(2-Acetoxybenzoyloxy)-4-(trimethylammonio)-butyric acid betaine:

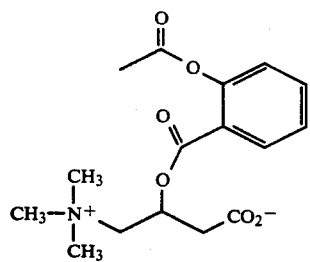

or a pharmaceutically acceptable salt thereof.

2. R-(−)-3-(2-Acetoxybenzoyloxy)-4-(trimethylammonio)-butyric acid betaine:

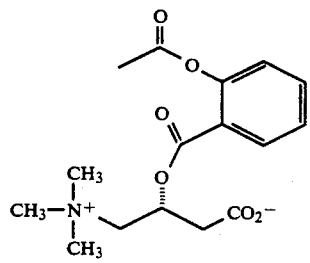

or a pharmaceutically acceptable salt thereof.

3. S-(+)-3-(2-Acetoxybenzoyloxy)-4-(trimethylammonio)-butyric acid betaine:

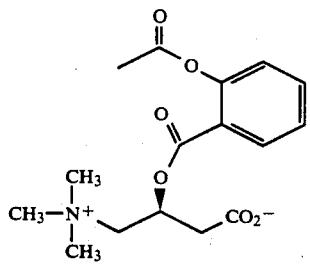

or a pharmaceutically acceptable salt thereof.

4. Process comprising administering a pharmaceutical composition containing 3-(2-acetoxybenzoyloxy)-4-(trimethylammonio)-butyric acid betaine and its pharmaceutically acceptable salts for use as therapeutic active analgesic ingredient and water as a carrier.

5. Process according to claim 4, comprising administering a pharmaceutical composition containing R-(−)-3-(2-acetoxybenzoyloxy)-4-(trimethylammonio)-butyric acid betaine or a pharmaceutically acceptable salt thereof as a therapeutically active analgesic ingredient and water as a carrier.

6. Process according to claim 4, comprising administering a pharmaceutical composition containing S-(+)-3-(2-acetoxybenzoyloxy)-4-(trimethylammonio)-butyric acid betaine or a pharmaceutically acceptable salt thereof as a therapeutically active analgesic ingredient and water as a carrier.

7. Process comprising administering a pharmaceutical composition containing 3-(2-acetoxybenzoyloxy)-4-(trimethylammonio)-butyric acid betaine or a pharmaceutically acceptable salt thereof as an analgesic.

8. Process according to claim 7, comprising administering a pharmaceutical composition containing (R)-(−)-3-(2-acetoxybenzoyloxy)-4-(trimethylammonio)-butyric acid betaine or a pharmaceutically acceptable salt thereof as an analgesic.

9. Process according to claim 7, comprising administering a pharmaceutical composition containing (S)-(+)-3-(2-acetoxybenzoyloxy)-4-(trimethylammonio)-butyric acid betaine or a pharmaceutically acceptable salt thereof as an analgesic.

10. Process for the production of 3-(2-acetoxybenzoyloxy)-4-(trimethylammonio)-butyric acid betaine comprising acetylating 3-(2-hydroxybenzoyloxy)-4-(trimethylammonio)-butyric acid betaine.

11. Process according to claim 10 wherein acetyl chloride or acetic anhydride in the presence of catalytic amounts of $H_2SO_4$ is used as the acetylation agent.

12. Process according to claim 11 wherein the acetylation is performed at a temperature between 40° and 100° C.

13. Process according to claim 10 wherein the acetylation is performed at a temperature between 40° and 100° C.